United States Patent [19]

Kristiansen et al.

[11] Patent Number: 5,179,094
[45] Date of Patent: Jan. 12, 1993

[54] PEST CONTROL AGENTS

[75] Inventors: Odd Kristiansen, Möhlin, Switzerland; Manfred Böger, Weil am Rhein, Fed. Rep. of Germany; Haukur Kristinsson, Basel; Peter Maienfisch, Aesch, both of Switzerland

[73] Assignee: Ciba-Geigy Corporation, Ardsley, N.Y.

[21] Appl. No.: 672,763

[22] Filed: Mar. 19, 1991

Related U.S. Application Data

[63] Continuation of Ser. No. 501,696, Mar. 29, 1990, abandoned.

Foreign Application Priority Data

Apr. 6, 1989 [CH] Switzerland .................. 1275/89

[51] Int. Cl.$^5$ .................. C07D 253/06; A01N 43/707
[52] U.S. Cl. .................. 514/242; 544/182
[58] Field of Search .................. 544/182; 514/242

[56] References Cited

U.S. PATENT DOCUMENTS 4,723,988 2/1988 Shapiro .................. 544/182
4,931,439 6/1990 Kristinsson .................. 514/242

FOREIGN PATENT DOCUMENTS 314615 5/1989 European Pat. Off. .

*Primary Examiner*—John M. Ford
*Attorney, Agent, or Firm*—Kevin T. Mansfield; Edward McC. Roberts

[57] ABSTRACT

There are disclosed novel substituted N-amino-1,2,4-triazinones of formula I

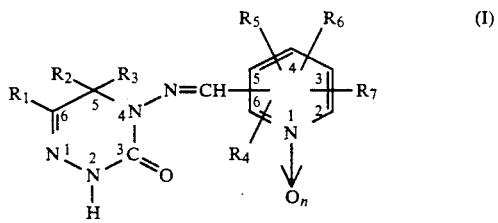

wherein
$R_1$ is $C_1$–$C_{12}$alkyl or $C_3$–$C_7$cycloalkyl,
$R_2$ and $R_3$ are each independently of the other hydrogen or $C_1$–$C_6$alkyl,
$R_4$, $R_5$, $R_6$ and $R_7$ are each independently of one another hydrogen, halogen, $C_1$–$C_3$alkyl,

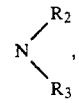

$C_1$–$C_3$alkoxy or $C_1$–$C_3$alkylthio, and n is 0 or 1, or a salt thereof, with the proviso that n is 1, if simultaneously the pyridine ring is attached via the 3-position to the methylidene group and $R_4$, $R_5$, $R_6$ and $R_7$ are each hydrogen; their use in pest control and pesticidal compositions which contain a compound of formula I as active component. The preferred utility is the control of pests of animals and plants.

16 Claims, No Drawings

PEST CONTROL AGENTS

This application is a continuation of application Ser. No. 501,696, filed Mar. 29, 1990 now abandoned.

The present invention relates to novel insecticidal N-amino-1,2,4-triazinones, to their preparation and to intermediates for their preparation, to compositions which contain said aminotriazines, and to the use thereof in pest control.

The aminotriazines of this invention have the formula I

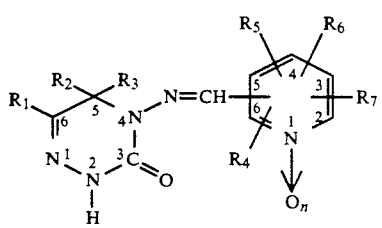

wherein
$R_1$ is $C_1-C_{12}$alkyl or $C_3-C_7$cycloalkyl,
$R_2$ and $R_3$ are each independently of the other hydrogen or $C_1-C_6$alkyl,
$R_4$, $R_5$, $R_6$ and $R_7$ are each independently of one another hydrogen, halogen, $C_1-C_3$alkyl,

$C_1-C_3$alkoxy or $C_1-C_3$alkylthio, and n is 0 or 1, and to the salts thereof, with the proviso that n is 1, if simultaneously the pyridine ring is attached via the 3-position to the methylidene group and $R_4$, $R_5$, $R_6$ and $R_7$ are each hydrogen.

The compounds of formula I can also be obtained in the form of acid addition salts. Suitable acids for forming such salts are organic and inorganic acids, for example hydrochloric acid, hydrobromic acid, nitric acid, different phosphoric acids, sulfuric acid, acetic acid, propionic acid, butyric acid, valeric acid, oxalic acid, malonic acid, maleic acid, fumaric acid, lactic acid, tartaric acid or salicyclic acid.

The alkyl groups by themselves or as moieties of other substituents may be straight-chain or branched. Typical of such alkyl groups are methyl, ethyl, propyl, isopropyl, butyl, isobutyl, sec-butyl, tert-butyl or pentyl, hexyl, octyl, decyl, dodecyl and the like, and the isomers thereof.

Suitable alkoxy and alkylthio groups may be straight-chain or branched and are e.g., typically, methoxy, methylthio, ethoxy, ethylthio and propoxy.

Cycloalkyl groups may be e.g., cyclopropyl, cyclobutyl, cyclopentyl or cyclohexyl.

Halogens are suitably fluoro and chloro and also bromo and iodo. Preferred halogens are fluoro and chloro.

Preferred compounds of formula I are those wherein $R_1$ is $C_1-C_4$alkyl; those wherein $R_1$ is methyl, ethyl, isopropyl or cyclopropyl; and those wherein n is 1.

Also preferred are the compounds of formula Ia

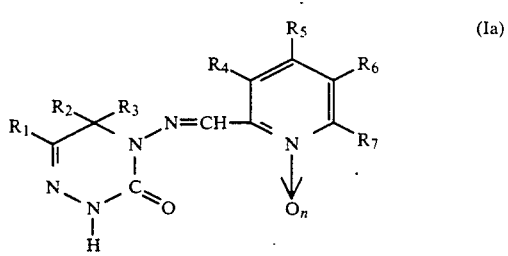

wherein $R_1$ to $R_7$ have the above given meanings.

In formulae I and Ia above, the substituents $R_2$ and $R_3$ are conveniently each independently of the other hydrogen or methyl, preferably hydrogen.

Among the compounds of formula I, those of formula Ib

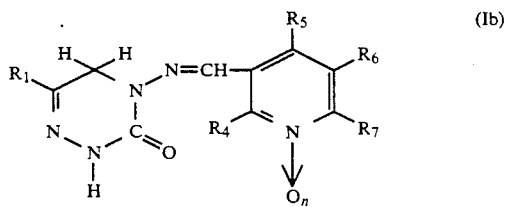

wherein $R_1$, $R_4$ to $R_7$ and n are as defined above, may also be highlighted.

On account of their biological activity, those compounds of formula Ib are preferred in which $R_1$ is methyl or ethyl, $R_5$ is hydrogen, $R_4$, $R_6$ and $R_7$ are each independently of one another chloro, methyl, methoxy or amino.

Particularly preferred compounds of this invention are those of formulae I, Ia and Ib wherein $R_6$ is hydrogen; or wherein $R_4$, $R_5$, $R_6$ and $R_7$ are hydrogen and n is 1; or wherein $R_1$ is methyl.

Further preferred compounds of formula Ib are those in which $R_4$, $R_5$ and $R_6$ are each independently of one another methyl or fluoro and $R_7$ is hydrogen, methylthio or dimethylamino, and n is 0.

Among the compounds of formula I, those compounds of formula Ic

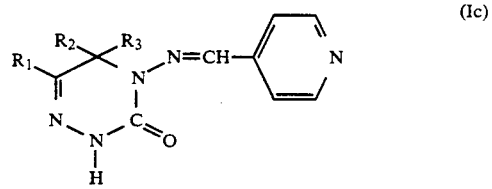

wherein $R_1$, $R_2$ and $R_3$ are as defined above, also merit special mention.

On account of its biological activity, 2,3,4,5-tetrahydro-3-oxo-4-[(pyridin-N-oxide-3-yl)methyleneimino]-6-methyl-1,2,4-triazine of formula

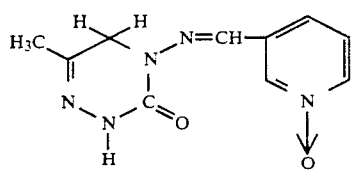

is to be singled out for special mention.

The compounds of formula I can be prepared by processes which are known per se, for example by reacting an aminotriazinone of formula II

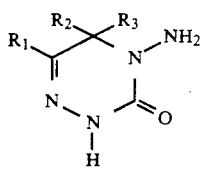

wherein
$R_1$ is $C_1$-$C_{12}$alkyl or $C_3$-$C_7$cycloalkyl,
$R_2$ and $R_3$ are each independently of the other hydrogen or $C_1$-$C_6$alkyl,
with an aldehyde of formula III

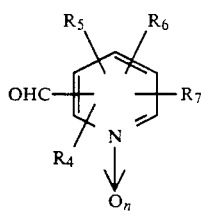

wherein
$R_4$, $R_5$, $R_6$ and $R_7$ are each independently of one another hydrogen, halogen, $C_1$-$C_3$alkyl,

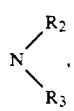

$C_1$-$C_3$alkoxy or $C_1$-$C_3$alkylthio, and n is 0 or 1, with the proviso that n is 1, if simultaneously the pyridine ring is attached via the 3-position to the methylidene group and $R_4$, $R_5$, $R_6$ and $R_7$ are each hydrogen, and isolating the reaction product. If desired, the resultant compounds can be converted into their salts in conventional manner.

The process is ordinarily carried out under normal pressure in the presence of a catalytic amount of a strong acid and in a solvent. The reaction temperature is in the range from +10° to 100° C., preferably from +40° to 80° C. Suitable acids are strong inorganic acids such as mineral acids, preferably hydrochloric acid. Suitable solvents are alcohols, ethers and ethereal compounds, nitriles or also water.

The starting aminotriazinones of formula II are known or can be prepared in a manner which is known per se, for example by cyclic rearrangement with hydrazine hydrate, i.e. reacting an oxadiazolone of formula IV

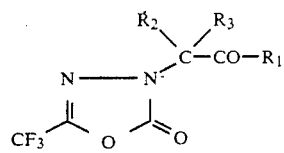

with hydrazine hydrate ($H_2N$—$NH_2.H_2O$), wherein $R_1$, $R_2$ and $R_3$ are as defined above. The process for the preparation of the aminotriazinones of formula II is ordinarily carried out under normal pressure and with or without a solvent. The reaction temperature is in the range from +15° to 120° C., preferably from +20° to 80° C. Suitable solvents are typically water, nitriles such as acetonitrile, alcohols, dioxane or tetrahydrofuran.

The above mentioned oxadiazolones of formula IV can be prepared by processes which are known per se, for example by reacting 5-trifluoromethyl-1,3,4-oxadiazol-2(3H)-one of formula V

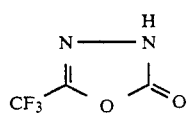

with a ketone of formula VI

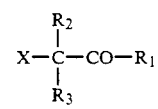

in which formulae the substituents $R_1$, $R_2$ and $R_3$ are as defined above and X is halogen. The process for the preparation of the oxadiazolones of formula IV is carried out under normal pressure and in the presence of a base and in a solvent. The reaction temperature is in the range from 0° to +150° C., preferably from +20° to 100° C. Suitable bases are organic and inorganic bases such as trimethylamine, alcoholates, sodium hydroxide or sodium hydride. Suitable solvents are typically alcohols, halogenated hydrocarbons such as chloroform, nitriles such as acetonitrile, tetrahydrofuran, dioxane, dimethyl sulfoxide or also water.

Among the aminotriazinones of formula II, 4-amino-6-phenyl-1,2,4-triazin-3-one is known (Liebigs Annalen der Chemie, 749, 125 (1971), i.e. the compound of formula II in which $R_1$ is phenyl, and $R_2$ and $R_3$ are each hydrogen. The compounds of formulae V and VI are known or can be prepared by processes which are known per se. The aldehydes of formula III, wherein n is 0, are known or can be prepared by processes which are known per se [Z. Chemie 184 (1970), J. Org. Chem. 46, 4836 (1981), Eur. J. Med. Chem. 12, 531 (1977), Heterocycles 26, 4836 (1981), J. Org. Chem. 53, 5320 (1988)]. The compounds of formula III (n=1) are usually prepared starting from the corresponding aldehyde (n=0) by reaction with a suitable oxidising agent such as m-chloroperbenzoic acid, whereby the aldehyde group is temporarily protected with a suitable protective group. To this end the aldehyde group can, for example, be acetylised.

The process of this invention is suitable for the preparation of compounds of formula I using pyridine derivatives (n=0) as well as pyridine-N-oxides (n=1) as starting materials. Depending on the desired final compound, a suitable free pyridine aldehyde (n=0) or the N-oxide thereof (n=1) is used.

It has now been found that the instant compounds of formula I are better tolerated by warm-blooded animals and have greater stability than known phosphoric acid esters and carbamates, while being well tolerated by plants. They are therefore most suitable for use as pest control agents, especially for controlling pests of plants, in particular insects.

The compounds of formula I are particularly suitable for controlling insects of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera, as well as representatives of the order Acarina.

Most particularly, plant-injurious insects, especially plant-injurious insects in ornamentals and crops of useful plants, in particular in cotton, vegetable, rice and fruit crops, can be controlled with the compounds of formula I. In this connection, particular attention is drawn to the fact that the compounds of formula I have a strongly pronounced systemic as well as contact action against sucking insects, especially against insects of the Aphididae family (e.g. against Aphis fabae, Aphis craccivora, Myzus persicae and Bemisia tabaci) which can only be controlled with difficulty using known pesticides.

The good pesticidal activity of the compounds of formula I corresponds to a mortality of at least 50-60% of the above pests.

The activity of the compounds employed and of the compositions containing them can be substantially broadened and adapted to prevailing circumstances by addition of other insecticides and/or acaricides. Examples of suitable additives include: organophosphorus compounds, nitrophenols and derivatives thereof, formamidines, ureas, carbamates, pyrethroids, chlorinated hydrocarbons, and Bacillus thuringiensis preparations.

The compounds of formula I are used as pest control agents in unmodified form, or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the compositions, the methods of application such as spraying, atomising, dusting, scattering or pouring, are chosen in accordance with the intended objectives and the prevailing circumstances.

The formulations, i.e. the compositions, preparations or mixtures containing the compound (active ingredient) of formula I or combinations thereof with other insecticides or acaricides, and, where appropriate, a solid or liquid adjuvant, are prepared in known manner, e.g. by homogeneously mixing and/or grinding the active ingredients with extenders, e.g. solvents, solid carriers and, in some cases, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethyl formamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. To improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Depending on the nature of the compound of formula I to be formulated, or of combinations thereof with other insecticides or acaricides, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$-$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and generally contain a $C_8$-$C_{22}$-alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing about 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphated adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil thioxilate, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substitutents, unsubstituted or halogenated lower alkyl, benzyl or hydroxylower alkyl radicals. The salts are preferably in the form of halides, methylsulfates or ethylsulfates, e.g. stearyltrimethylammonium chloride or benzyl bis(2-chloroethyl)ethylammonium bromide.

The surfactants customarily employed in the art of formulation are described e.g. in the following publications "McCutcheon's Detergents and Emulsifiers Annual", MC Publishing Corp., Ridgewood, N.J., 1979; Dr. Helmut Stache, "Tensid Taschenbuch" (Handbook of Surfactants), Carl Hanser Verlag, Munich/Vienna, 1981.

The pesticidal compositions usually contain 0.1 to 99%, preferably 0.1 to 95%, of a compound of formula I, 1 to 99.9% of a solid or liquid adjuvant, and 0 to 25%, preferably 0.1 to 25%, of a surfactant, the percentages being by weight.

Whereas commercial products are preferably formulated as concentrates, the end user will normally employ diluted formulations of substantially lower concentration, for example 0.1 to 1000 ppm. In general, the concentration of compound of formula I—especially for crop areas—is 0.025 to 1.0 kg/ha, preferably 0.1 to 0.5 kg/ha, for example 0.1 to 0.25 kg/ha.

The compositions may also contain further ingredients, such as stabilisers, antifoams, viscosity regulators, binders, tackifiers as well as fertilisers or other chemical agents for obtaining special effects.

EXAMPLES

1. Preparation of the Compounds of Formula I and their Intermediates

Example H1:2-Oxo-5-trifluoromethyl-2,3-dihydro-1,3,4-oxadiazole-1-3-acetone 15 g (0.5 mol) of an 80% dispersion of NaH in oil are washed free of oil with petroleum ether and added to 125 ml of dimethyl formamide. Then 77 g (0.5 mol) of 5-trifluoromethyl-1,3,4-oxadiazole-2(3H)-one in 250 ml of dimethyl formamide are added dropwise to this suspension at room temperature over 1 hour, and the mixture is stirred for 3 hours. After addition of 55.5 g (0.6 mol) of chloroacetone, the reaction mixture is stirred for 16 hours at room temperature and then concentrated by evaporation. Upon addition of 1000 ml of water to the residue, the solid precipitate is filtered with suction and dried, to give the title compound of formula

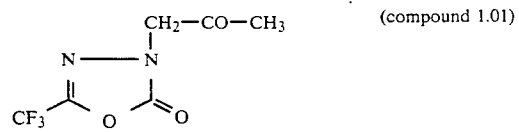
(compound 1.01)

in the form of a colourless solid; m.p. 85° C. (yield: 96 g; 91.7%).

The following compounds of formula IV are prepared in analogous manner.

TABLE 1

(IV)

| Compound | $R_1$ | $R_2$ | $R_3$ | Physical data |
|---|---|---|---|---|
| 1.01 | $CH_3$ | H | H | m.p. 85° C. |
| 1.02 | i-$C_3H_7$ | H | H | m.p. 74–75° C. |
| 1.03 | $C(CH_3)_3$ | H | H | m.p. 67° C. |
| 1.04 | $C_6H_5$ | H | H | m.p. 100–102° C. |
| 1.05 | $CH_3$ | $CH_3$ | H | oil |
| 1.06 | $CH_3$ | $CH_3$ | $CH_3$ | oil |
| 1.07 | $C_2H_5$ | H | H | m.p. 76–77° C. |
| 1.08 | △ | H | H | m.p. 77–78° C. |
| 1.09 | H | H | H | |
| 1.10 | $C_2H_5$ | $CH_3$ | H | |
| 1.11 | n-$C_3H_7$ | H | H | |
| 1.12 | △ | $CH_3$ | H | |
| 1.13 | H | $CH_3$ | H | |
| 1.14 | i-$C_3H_7$ | $CH_3$ | H | |
| 1.15 | i-$C_3H_7$ | $CH_3$ | $CH_3$ | |
| 1.16 | $C(CH_3)_3$ | $CH_3$ | H | |
| 1.17 | $CH_3$ | $C_2H_5$ | H | |
| 1.18 | $CH_3$ | $C_2H_5$ | $CH_3$ | |
| 1.19 | △ | $CH_3$ | $CH_3$ | |
| 1.20 | △ | $C_2H_5$ | $CH_3$ | |

Example H2:2,3,4,5-Tetrahydro-3-oxo-4-amino-6-methyl-1,2,4-triazine

With cooling, 210 g (1.0 mol) of 2-oxo-5-trifluoromethyl-2,3-dihydro-1,3,4-oxadiazole-3-acetone are added to 250 ml of hydrazine hydrate. The resultant clear brown solution is stirred for 2 hours and then concentrated by evaporation under vacuum. The residue is chromatographed over silica gel (elution with a 9:1 mixture of methylene chloride/methanol), and the solvent is removed by evaporation. The title compound of formula

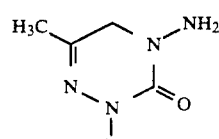
(compound 2.01)

crystallises from the residual oil after addition of ether, m.p. 117°-119° C. (yield: 64 g; 50%).

The following compounds of formula II are prepared in analogous manner:

TABLE 2

(II)

| Compound | $R_1$ | $R_2$ | $R_3$ | m.p. °C. |
|---|---|---|---|---|
| 2.01 | $CH_3$ | H | H | 117–119 |
| 2.02 | $CH_3$ | $CH_3$ | H | 172–174 |
| 2.03 | $CH_3$ | $CH_3$ | $CH_3$ | 138–139 |
| 2.04 | $C_2H_5$ | H | H | 143–145 |
| 2.05 | $i-C_3H_7$ | H | H | 79–81 |
| 2.06 | $C(CH_3)_3$ | H | H | 148–150 |
| 2.07 | △ | H | H | 94–95 |
| 2.08 | $C_6H_5$ | H | H | 199–202 |
| 2.09 | $4-Cl-C_6H_4$ | H | H | 208–210 |
| 2.10 | H | H | H | |
| 2.11 | $CH_3$ | $C_2H_5$ | H | |
| 2.12 | $C_2H_5$ | $CH_3$ | $CH_3$ | |
| 2.13 | $C_2H_5$ | $CH_3$ | H | |
| 2.14 | $n-C_3H_7$ | H | H | |
| 2.15 | $n-C_3H_7$ | $CH_3$ | H | |
| 2.16 | $n-C_3H_7$ | $CH_3$ | $CH_3$ | |
| 2.17 | $i-C_3H_7$ | $CH_3$ | H | |
| 2.18 | $C(CH_3)_3$ | $CH_3$ | H | |
| 2.19 | $C(CH_3)_3$ | $CH_3$ | $CH_3$ | |
| 2.20 | △ | $CH_3$ | $CH_3$ | |
| 2.21 | △ | $CH_3$ | H | |

Example H3:
2,3,4,5-Tetrahydro-3-oxo-4-[(2-methylpyridin-3-yl)-methyleneamino]-6-methyl-1,2,4-triazine To a solution of 0.5 g (4 mmol) of 2,3,4,5-tetrahydro-3-oxo-4-amino-6-methyl-1,2,4-triazine in 250 ml of ethanol are added, at room temperature, 0.48 g (4 mmol) of 2-methylpyridine-3-carbaldehyde and 1 drop of concentrated HCl. The reaction mixture is stirred for ½ hour and then filtered. The isolated solid is washed with ether and dried, affording the title compound of formula

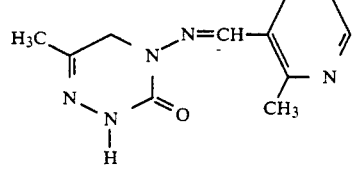

(compound 4.19)

in the form of a colourless solid; m.p. 226°-229° C. (yield: 0.6 g; 64%).

Example H4:
2,3,4,5-tetrahydro-3-oxo-4-[(pyridin-N-oxide-3-yl)-methyleneamino]-6-methyl-1,2,4-triazine To a solution of 2.56 g (0.02 mol) 2,3,4,5-tetrahydro-3-oxo-4-amino-6-methyl-1,2,4-triazine in 25 ml of ethanol are added 2.44 g (0.02 mol) of pyridine-3-carbaldehyde-N-oxide. The reaction mixture is refluxed for ½ hour, then cooled, and the precipitated solid is isolated by filtration, washed with ether and dried. The title compound of formula

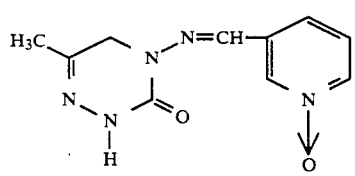

(compound 4.09)

is obtained in the form of a white solid; m.p. 242°-244° C. (yield: 3.6 g; 84%).

The following compounds of formulae Ia, Ib and Ic are also prepared as described above:

TABLE 3

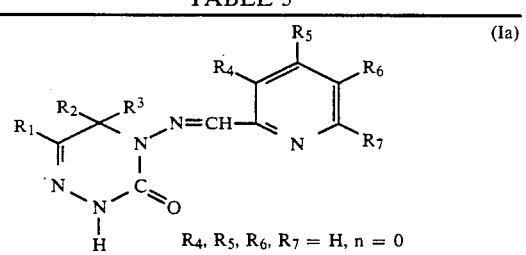

(Ia)

$R_4, R_5, R_6, R_7 = H, n = 0$

| Compound | $R_1$ | $R_2$ | $R_3$ | Physical data |
|---|---|---|---|---|
| 3.01 | $CH_3$ | H | H | m.p. 249–250° C. |
| 3.02 | $CH_3$ | $CH_3$ | $CH_3$ | m.p. 162–163° C. |

TABLE 4

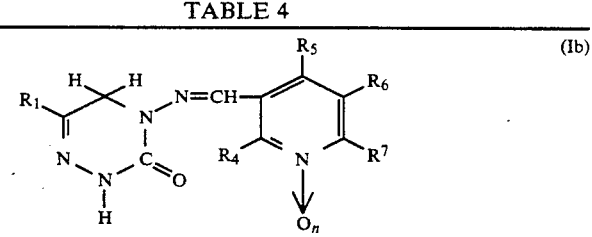

(Ib)

| Compound | $R_1$ | $R_4$ | $R_5$ | $R_6$ | $R_7$ | n | Physical data |
|---|---|---|---|---|---|---|---|
| 4.01 | $CH_3$ | H | H | H | Cl | 0 | m.p. 227–228° C. |
| 4.02 | $CH_3$ | Cl | H | Cl | Cl | 0 | m.p. 248–249° C. |
| 4.03 | $C_2H_5$ | H | H | H | Cl | 0 | m.p. 226–227° C. |
| 4.04 | $CH_3$ | H | H | H | $CH_3O$ | 0 | m.p. 193–196° C. |
| 4.05 | $CH_3$ | $CH_3O$ | H | H | $CH_3O$ | 0 | m.p. 241–243° C. |
| 4.06 | $CH_3$ | Cl | H | H | H | 0 | m.p. 240–241° C. |

TABLE 4-continued

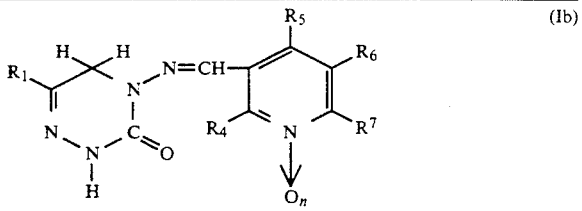

| Compound | $R_1$ | $R_4$ | $R_5$ | $R_6$ | $R_7$ | n | Physical data |
|---|---|---|---|---|---|---|---|
| 4.07 | $CH_3$ | H | H | H | $CH_3$ | 0 | m.p. 220–223° C. |
| 4.08 | $CH_3$ | $NH_2$ | H | H | H | 0 | m.p. >250° C. |
| 4.09 | $CH_3$ | H | H | H | H | 1 | m.p. 242–244° C. |
| 4.10 | $CH_3$ | H | H | $CH_3$ | H | 0 | m.p. 229–230° C. |
| 4.11 | $CH_3$ | H | $CH_3$ | H | H | 0 | |
| 4.12 | $CH_3$ | H | H | F | H | 0 | |
| 4.13 | $CH_3$ | F | H | H | H | 0 | |
| 4.14 | $CH_3$ | H | H | H | F | 0 | |
| 4.15 | $CH_3$ | H | F | H | H | 0 | |
| 4.16 | $CH_3$ | H | H | H | $CH_3S$ | 0 | |
| 4.17 | $CH_3$ | H | H | H | $(CH_3)_2N$ | 0 | |
| 4.18 | $CH_3$ | $CH_3$ | H | H | H | 1 | m.p. 238–240° C. |
| 4.19 | $CH_3$ | $CH_3$ | H | H | H | 0 | m.p. 226–229° C. |
| 4.20 | $CH_3$ | $SCH_3$ | H | H | H | 0 | m.p. 225° C. |
| 4.21 | $C_4H_9(t)$ | H | H | H | H | 1 | m.p. 129–132° C. |
| 4.22 | $C_3H_7(i)$ | H | H | H | H | 1 | m.p. 120–121° C. |

TABLE 5

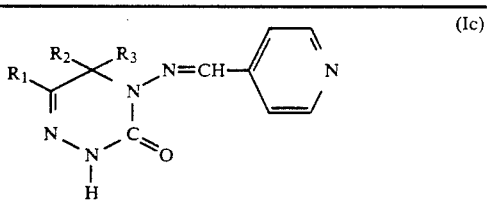

| Compound | $R_1$ | $R_2$ | $R_3$ | Physical data |
|---|---|---|---|---|
| 5.01 | $CH_3$ | H | H | m.p. 242° C. |
| 5.02 | $(CH_3)_2CH$ | H | H | m.p. 168–170° C. |
| 5.03 | $CH_3$ | $CH_3$ | $CH_3$ | m.p. 234–235° C. |

EXAMPLE 2: FORMULATION EXAMPLES

Formulations for Compounds of Formula I or Combinations Thereof with other Insecticides or Acaricides (Throughout, Percentages ary by Weight)

| F1. Wettable powders | a) | b) | c) |
|---|---|---|---|
| compound of formula I or combination | 25% | 50% | 75% |
| sodium ligninsulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 mol of ethylene oxide) | — | 2% | — |
| highly dispersed silicic acid | 5% | 10% | 10% |
| kaolin | 62% | 27% | — |

The active ingredient or combination is thoroughly mixed with the adjuvants and the mixture is thoroughly ground in a suitable mill, affording wettable powders which can be diluted with water to give suspensions of the desired concentration.

| F2. Emulsifiable concentrate | |
|---|---|
| compound of formula I or combination | 10% |
| octylphenol polyethylene glycol ether (4–5 mol of ethylene oxide) | 3% |
| calcium dodecylbenzenesulfonate | 3% |
| castor oil polygycol ether (36 mol of ethylene oxide) | 4% |
| cyclohexanone | 30% |
| xylene mixture | 50% |

Emulsions of any required concentration can be obtained from this concentrate by dilution with water.

| F3. Dusts | a) | b) |
|---|---|---|
| compound of formula I or combination | 5% | 8% |
| talcum | 95% | — |
| kaolin | — | 92% |

Ready for use dusts are obtained by mixing the active ingredient with the carrier, and grinding the mixture in a suitable mill.

| F4. Extruder granulate | |
|---|---|
| compound of formula I or combination | 10% |
| sodium ligninsulfonate | 2% |
| carboxymethylcellulose | 1% |
| kaolin | 87% |

The active ingredient or combination is mixed and ground with the adjuvants, and the mixture is subsequently moistened with water. The mixture is extruded and then dried in a stream of air.

| F5. Coated granulate | |
|---|---|
| compound of formula I or combination | 3% |
| polyethylene glycol (mol. wt. 200) | 3% |
| kaolin | 94% |

The finely ground active ingredient or combination is uniformly applied, in a mixer, to the kaolin moistened with polyethylene glycol. Non-dusty coated granulates are obtained in this manner.

| F6. Suspension concentrate | |
| --- | --- |
| compound of formula I or combination | 40% |
| ethylene glycol | 10% |
| nonylphenol polyethylene glycol ether (15 mol of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient or combination is intimately mixed with the adjuvants, giving a suspension concentrate from which suspensions of any desired concentration can be obtained by dilution with water.

3. BIOLOGICAL EXAMPLES

Example B.1: Contact action against *Aphis craccivora*

Before the start of the test, 4- to 5-day-old pea seedlings (*Pisum satirum*) reared in pots are each populated with about 200 insects of the species *Aphis craccivora*. The treated plants are sprayed direct to drip point 24 hours later with an aqueous formulation containing 400 ppm of the test compound. Two plants are used for each test compound, and a mortality count is made after a further 24 and 72 hours. The test is carried out at 21°-22° C. and a relative humidity of about 55%.

Compounds according to Tables 3, 4 and 5 exhibit good activity in this test.

Example B.2: Systemic action against *Myzus persicae*

Pimenta plants are infected with well populated pea seedlings. The soil is treated 4 days later with 25 ml of a 0.1% spray mixture prepared from a 10% emulsifiable concentrate and water, such that the concentration of test compound in the soil is 12.5 ppm (amount by weight, based on the volume of the soil). The plants are enveloped in a paper frill.

Evaluation of mortality is made 3 and 7 days after the start of the test. Two plants, each in a separate pot, are used for each test compound. The test is carried out at 25° C. and ca. 65% relative humidity.

After 1, 2 and 4 weeks the plants are populated anew and fresh mortality counts are made after 3 and 7 days following treatment.

Compounds according to Tables 3, 4 and 5 exhibit good activity in this test.

Example B.3: Contact action against *Myzus persicae*, direct spray test 4 days before treatment, pipmenta plants (in the 6-leaf stage, in pots) are infested with a population of *Myzus persicae* (R strain) by placing pea seedlings 2-3 cm long and well populated with aphids on the pimenta plants. As soon as the pea seedlings begin to wither, the aphids migrate onto the test plants (pimenta). The treated plants are sprayed direct to drip point 24 hours later with an aqueous suspension prepared from a 25% wettable powder, containing 100 ppm of the test compound. Four plants are used for each test compound. A mortality count is made 7 days after application. The test is carried out at 21°-22° C. and ca. 60% relative humidity.

The compounds according to Tables 3, 4 and 5 exhibit good activity in this test. In particular, compound 4.09 effects over 80% kill.

Example B.4: Test of long-term action against *Myzus persicae*

Peperoni plants (in the 6-leaf stage, in pots) are treated by spray application with the test solutions and, 2 days after the treatment, the test plants are infested with a population of Myzus persicae (R strain) as described in Example B.3. An evaluation of the percentage mortality is made 5 days after populating the plants.

The compounds according to Tables 3, 4 and 5 exhibit good activity against myzus persicae in this test. In particular compound 4.09 effects over 80% kill.

Example B.5: Contact action against *Bemisia tabaci*

Bean plants in pots (*Phaseolus vulgaris*, Autan variety) are populated in the 2-leaf stage with Bemisia tabaci (40 adults per plant). After a 3-day period for oviposition, the adults are removed. Ten days after population, when ca. ⅔ of the nymphs are in the late first nymphal stage and ⅓ are already in the second nymphal stage, the plants are treated in a spray chamber with a spray mixture (prepared from a 10% emulsifiable concentrate and water) in different concentrations.

A count of dead nymphs, pupae and adults of the $F_1$ generation is made 24 days after population. The test is carried out at 25° C. and 50–60% relative humidity.

Compounds according to Tables 3, 4 and 5 exhibit good activity at a concentration of 3 ppm. In particular, compound 4.09 effects over 80% kill.

What is claimed is:

1. A compound of formula I

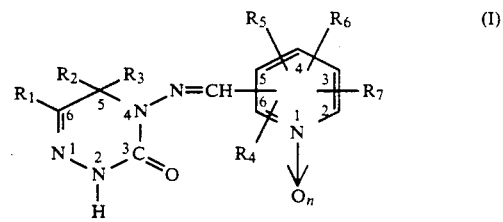

wherein $R_1$ is $C_1$-$C_{12}$alkyl or $C_3$-$C_7$cycloalkyl, $R_2$ and $R_3$ are each independently of the other hydrogen or $C_1$-$C_6$alkyl, $R_4$, $R_5$, $R_6$ and $R_7$ are each independently of one another hydrogen, halogen, $C_1$-$C_3$alkyl,

$C_1$-$C_3$alkoxy or $C_1$-$C_3$alkylthio, and n is 1, or a salt thereof.

2. A compound of formula I according to claim 1, wherein $R_1$ is $C_1$-$C_4$alkyl.

3. A compound of formula I according to claim 1, wherein $R_1$ is methyl, ethyl, isopropyl or cyclopropyl.

4. A compound of formula Ia according to claim 1

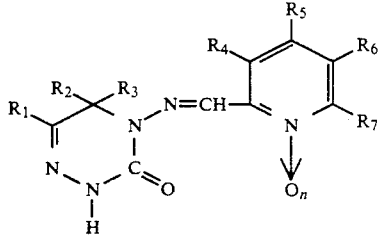

wherein $R_1$ to $R_7$ and n are as defined in claim 1.

5. A compound according to claim 1, wherein $R_2$ and $R_3$ are each independently of the other hydrogen or methyl.

6. A compound according to claim 3, wherein $R_2$ and $R_3$ are each independently of the other hydrogen.

7. A compound of formula Ib according to claim 1

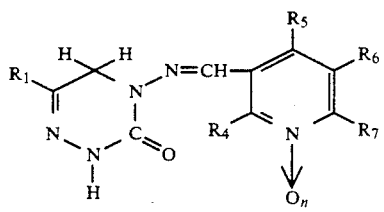

wherein $R_1$, $R_4$ and $R_7$ and n are as defined in claim 1.

8. A compound according to claim 1, wherein $R_1$ is methyl or ethyl, $R_5$ is hydrogen, $R_4$, $R_6$ and $R_7$ are each independently of one another chloro, methyl, methoxy or amino.

9. A compound according to claim 1, wherein $R_6$ is hydrogen.

10. A compound according to claim 1, wherein $R_4$, $R_5$, $R_6$ and $R_7$ are each hydrogen.

11. A compound according to claim 7, wherein $R_1$ is methyl.

12. 2,3,4,5-Tetrahydro-3-oxo-4-[(pyridin-N-oxide-3-yl)-methyleneimino]-6-methyl-1,2,4-triazine of formula

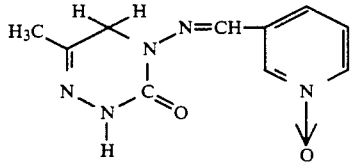

according to claim 11.

13. An insecticidal and arachnidicidal composition which contains, as active component, an effective amount of a compound of formula I as claimed in claim 1, together with a suitable carrier.

14. A method of controlling pests selected from insects and arachnids, which comprises contacting or treating said pests, their different development stages or the locus thereof, with and insecticidally or arachnidicidally effective amount of a compound of formula I as claimed in claim 1 or a salt thereof, or with a composition containing a pesticidally effective amount of such a compound.

15. A method according to claim 14, wherein the pests to be controlled are plant-injurious insects.

16. A method according to claim 15, wherein the pests to be controlled are sucking insects.

* * * * *